(12) United States Patent
Chopra

(10) Patent No.: US 6,300,377 B1
(45) Date of Patent: Oct. 9, 2001

(54) COENZYME Q PRODUCTS EXHIBITING HIGH DISSOLUTION QUALITIES

(76) Inventor: Raj K. Chopra, 704 Dermott Ct., Westbury, NY (US) 11590

( * ) Notice: Subject to any disclaimer, the term of this patent is extended or adjusted under 35 U.S.C. 154(b) by 35 days.

(21) Appl. No.: 09/790,783

(22) Filed: Feb. 22, 2001

(51) Int. Cl.[7] .................. A61K 31/075; A61K 31/355; A61K 31/34; A61K 31/205; A61K 31/20; A61K 31/07

(52) U.S. Cl. .................. 514/715; 514/458; 514/474; 514/556; 514/560; 514/725

(58) Field of Search .................. 514/458, 474, 514/556, 560, 715, 725

(56) References Cited

U.S. PATENT DOCUMENTS

| | | | |
|---|---|---|---|
| 4,869,900 | * | 9/1989 | Pozzi et al. .................. 424/94.1 |
| 5,977,162 | * | 11/1999 | Seidman .................. 514/440 |
| 6,184,255 | * | 2/2001 | Mae et al. .................. 514/720 |

* cited by examiner

Primary Examiner—Raymond Henley, III

(57) ABSTRACT

The present invention relates to a composition in liquid dosage form of coenzyme Q or ubiquinone which can be formulated into cosmetic, dietary supplement or pharmaceutical dosage form for administration to patients. The dosage form comprises an effective amount of coenzyme Q or ubiquinone ranging from about 0.05% to about 15%, more preferably about 1% to about 10.0% by weight of the composition in combination with a polysorbate surfactant such as a Tween™, surfactant, a vegetable oil or triglyceride, in further combination with a glyceryl ester in amounts effective to produce a liquid dosage form. Optional additives include a phospholipid such as hydroxylated lecithin, among others such as tocopherols or tocopherol esters effective to solubilize the ubiquinone in combination as well as other bioactive agents. Compositions according to the present invention avoid the inclusion of a polyhydric alcohol solvent in solubilizing amounts.

45 Claims, No Drawings

COENZYME Q PRODUCTS EXHIBITING HIGH DISSOLUTION QUALITIES

FIELD OF THE INVENTION

The present invention relates to compositions comprising coenzyme Q (ubiquinone) in liquid form which provides enhanced bioavailability and may be presented in dietary supplement, cosmetic or pharmaceutical dosage form (preferably oral dosage form), including hard or soft gelatin capsules for oral administration.

BACKGROUND OF THE INVENTION

Coenzyme Q (ubiquinone), a dietary supplement, is a vitamin-like substance which is used to treat congestive heart failure and other cardiac problems, including heart ailments and diseases such as congestive heart failure, as well as a number of other conditions including high blood pressure, mitochochondrial disorders, including mitochondrial encephalomyopathy, anoxia, lactic acidosis, strokelike symptoms, neurodegenerative diseases, Kearns-Sayre syndrome and Alper's disease, among others. Coenzyme Q is the best known of a group of lipophilic quinones which have the capacity to transfer reducing equivalents or electrons within a lipid phase of cellular membranes. Reduced benzoquinones in general are effective reductants for oxygen or lipid radicals. Early studies showed that reduced coenzyme Q is an effective antioxidant. See, Mellors and Tappel, 1996, *J. Biol. Chem.*, 241: 4353–4356. Reduced coenzyme Q now appears to function as part of a complex chain of antioxidant activity.

An important role of coenzyme Q can be in reduction of radicals of α-tocopherol and ascorbate formed when these antioxidants are oxidized by oxygen or carboxyl radicals. There are no enzymes for direct reduction of tocopheryl radical or external ascorbate radical, but there are enzymes in all membranes which can reduce coenzyme Q and the reduced coenzyme Q can reduce the tocopheryl or ascorbate radicals to restore tocopherol or ascorbate. Without the support of enzymes to reduce coenzyme Q, the reduced coenzyme Q would not be a very effective antioxidant because the semiquinone formed by interaction with lipid or oxygen radicals is readily autooxidized with formation of a superoxide radical.

OBJECTS OF THE INVENTION

It is therefore an object of the present invention to provide a liquid form of coenzyme Q (ubiquinone) which can be administered with high bioavailability.

It is an additional object of the invention to provide a method for enhancing the bioavailability of coenzyme Q to patients by administering effective amounts of coenzyme Q in a liquid form which exhibits high bioavailability.

It is still another object of the present invention to provide coenzyme Q in liquid form which provides enhanced bioavailability and may be presented in dietary supplement, cosmetic or pharmaceutical dosage forms oral or topical administration.

These and/or other objects of the invention may be readily gleaned from a description of the invention which follows.

SUMMARY OF THE INVENTION

The present invention relates to a composition in cosmetic, dietary supplement or pharmaceutical dosage form of coenzyme Q which can be administered in high bioavailability form topically or as an oral dosage form. The compositions according to the present invention comprise an effective amount of coenzyme Q ranging from about 0.05% to about 15%, more preferably about 0.5% to about 10%, more preferably about 1.0% to about 7.5% by weight of the composition in combination with a polysorbate surfactant such as a Tween™ surfactant, most preferably, polysorbate 80, and amount of a vegetable oil or triglyceride, in further combination with an effective amount of a mono-, di or tri substituted glyceryl ester, preferably a $C_1$–$C_6$ glyceryl triester, even more preferably a $C_1$–$C_4$ glyceryl triester, or mixtures of these esters. In certain compositions according to the present invention, a component such as a phospholipid (e.g., hydroxylated lecithin) may be added to increase the solubility of the composition. In addition, in preferred embodiments according to the present invention, tocopherols (including vitamin E and vitamin E esters (such as vitamin E acetate, among others) or other vitamin additive, including other bioactive agents (lipophilic and non-lipophilic), are combined with ubiquinone as active agent. In addition, in certain embodiments, water may be optionally added, in an amount ranging from about 0.01% to about 10% by weight of the final formulation. Compositions according to the present invention preferably avoid the inclusion of a polyhydric alcohol solvent, such as propylene glycol or glycerine.

In addition to the above components, compositions according to the present invention may optionally comprise flavorings, preservatives and coloring agents in relatively minor amounts (i.e., in amounts which do not substantially impact the ability of the other components to work together to form a liquid dosage form). Compositions according to the present invention are preferably solvent free.

DETAILED DESCRIPTION OF THE INVENTION

The term "coenzyme Q" or "ubiquinone" is used throughout the present specification to describe a group of lipid soluble benzoquinones involved in electron transport in mitochondrial preparations, i.e., in the oxidation of succinate or reduced nicotine adenine dinucleotide (NADH) via the cytochrome system. According to the existing dual system of nomenclature, the compounds can be described as: coenzyme $Q_N$, where n is 1–12 or ubiquinone (x) in which x designates the total number of carbon atoms in the side chain and can be any multiple of 5. Differences in properties are due to to the difference in the chain length. The preferred ubiquinone for use in the present invention is coenzyme $Q_{10}$.

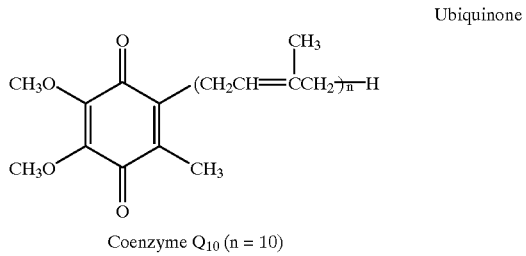

Ubiquinone

Coenzyme $Q_{10}$ (n = 10)

The amount of ubiquinone which is included in compositions according to the present invention ranges from about 0.05% to about 15% (preferably, no more than about 10.0% by weight and even more preferably no more than about 7.5% by weight of the final liquid composition).

The term "surfactant" or "emulsifier" is used interchangeably to describe additives to compositions according to the present invention. Surfactants for use in the present invention are solubilizers which are used to promote the solubility of the ubiquinone. These are to be used in combination with a triglyceride or vegetable oil and a short chain glyceryl ester, preferably a glyceryl triester. Polysorbate surfactants (Tween™) are clearly preferred. The amount of surfactant used in the present invention ranges from about 0.1% to about 50% by weight, more preferably about 1.5% to about 40%, preferably about 10% to about 35% by weight. Surfactants for use in the present invention are pharmaceutically acceptable and include, for example, the polysorbate surfactants as primary surfactants, and in certain embodiments, minor amounts of secondary surfactants such as the Span™ surfactants. Surfactants which exist in the liquid state at temperatures at or less than formulation temperature (generally, about 80° C. or less, more preferably about 50–65°) are preferred because they can also function as co-solvents or co-solubilizers in the present compositions. The preferred surfactant for use in the present invention is polysorbate 80 (Tween™80) surfactant.

In the present invention, the use of polysorbate (Tween™) 80 surfactant is preferred, with a mixture of Tween™ surfactants or Tween™ and Span™ surfactants, representing an alternative embodiment.

The Tween™ or polysorbate type surfactants are oleate esters of sorbitol and its anhydrides copolymerized with a number of moles of ethylene oxide per mole of sorbitol and sorbitol anhydride. The Tween™ surfactants are soluble or well dispersible in water. Preferred Tween™ surfactants include a sorbitan mono-9-octadecenoate poly(oxy-1,2-etheandiyl) derivative otherwise known as Tween™ 80 or Polysorbate 80.

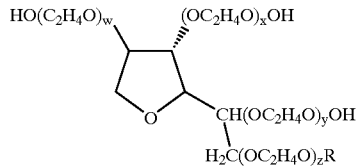

Polysorbate 80

The sum of w,x,y and z is 20 and R=$C_{17}H_{33}CO$

The Span™ surfactants, which may be optionally included in the present compositions of the present invention as secondary surfactants (the polysorbate surfactants are the preferred primary surfactants), are partial esters of common fatty acids, such as lauric acid, palmitic acid, stearic acid and oleic acids and hexitol anhydrides such as hexitans and hexides, derived from sorbitol (see below). In the case of Span 20, the sorbitan fatty ester is based upon laurate ester. In the case of Span 60, the ester is based upon stearate ester and in the case of Span 80, the ester is based upon oleic ester. The hydrophilic character of the Span™ surfactants is supplied by free hydroxyl and oxyethylene groups, while the lipophilic character is provided by the long chain fatty groups. The Span™ surfactants tend to be oil soluble and dispersible or insoluble in water. However, these surfactants work in tandem with the more water soluble polyhydric alcohol to provide a soluble ubiquinone for soft gel formulations according to the present invention. The use of Span 80 in formulating compositions according to the present invention may be optional.

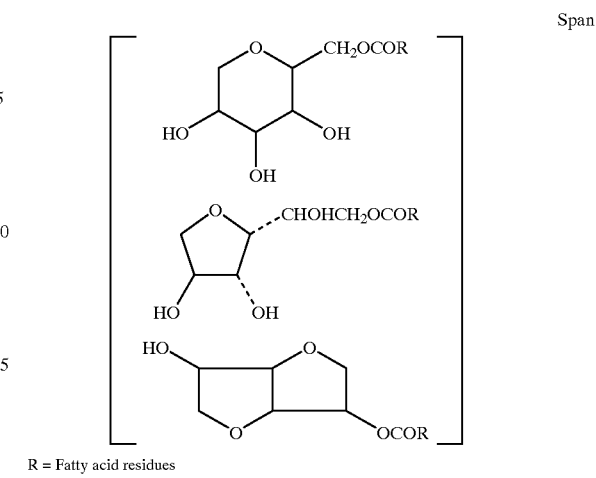

R = Fatty acid residues

The term "glyceryl ester" is used throughout the specification to describe a component of compositions according to the present invention which is included in effective amounts, in combination with the surfactant(s) and mono-, di- and triglycerides in order to solubilize ubiquinone. The term glyceryl ester embraces all short chain (i.e., $C_2$ to $C_7$) esters of glycerol, including mono-, di and triesters, with the di- and triesters being preferred and with $C_2$ to $C_5$ esters groups also being preferred (see structure below). Glyceryl triesters are most preferred, especially glyceryl triacetate and glyceryl tributyrate (tributyrin). Glyceryl esters are included in compositions according to the present invention in effective amounts, which preferably range from about 0. 1% to about 60% by weight, more preferably about 5% to about 30% by weight, even more preferably about 15% to about 25% by weight of the final composition. Exemplary triesters may be represented by the structure:

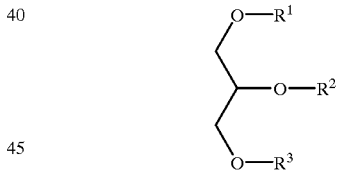

Glyceryl Ester where $R^1$, $R^2$ and $R^3$ are H or a $C_2$ to $C_7$ acyl group, preferably a $C_2$ to $C_5$ acyl group, with the proviso that at least one R is an acyl group, preferably all three are acyl groups. Most preferably, $R^1$, $R^2$ and $R^3$ are acetate groups (glyceryl triacetate) or a butyrate group (tributyrin or glyceryl tributyrate). In preferred aspects according to the present invention, especially where a glyceryl triester is used, there is no need to use a secondary surfactant and the present compositions may be formulated using one or more polysorbate surfactants, without a secondary surfactant or the requirement to include a polyhydric alcohol solvent.

The term "phospholipid" as used herein shall mean any suitable material of a lipid-like, but amphipathic nature which is a phospholipid, and which preferably has a hydrophobic chain at one end of the molecule and a hydrophilic, charged (anionic) portion at the other end of the molecule. Phospholipids are optionally used in the present invention to enhance solubility and dissolution properties of the final composition, especially where large amounts of ubiquinone and/or other lipophilic active agents are employed.

Hydroxylated phospholipids pursuant to the present invention are preferred. In the present invention, the phospholipid is used to aid in promoting the solubility of ubiquinone or other active agent in order to promote the bioavailability of the active(s). Although any number of phospholipids can be used in the present invention, preferred phospholipids include, for example, phosphatidylcholine (PC), phosphatidylethanolamine (PE), distearoylphosphatidylcholine (DSPC), phosphatidylserine (PS), phosphatidylglycerol (PG), phosphatidic acid (PA), phosphatidylinositol (PI), sphingomyelin (SPM), and the like, alone or in combination. The phospholipids can be synthetic or derived from natural sources such as egg or soy, but are preferably natural or are obtained from natural products. Some synthetic phospholipids which can be used in the present invention include, for example, dimyristoylphosphatidylcholine (DMPC) and dimyristoylphosphatidylglycerol (DMPG). Within the class of phospholipids include the phosphoglycerides, which are generally related to triglycerides in that they contain two fatty acid residues and a phosphate ester (generally, a diester) group off of the three hydroxyl groups of glycerine.

Phospholipids are optional in the present invention, but where they are included, they preferably are used in the present compositions in amounts effective to aid in promoting the solubility of ubiquinone and optionally, other lipophilic agents which may be included as optional agents in the compositions according to the present application. This amount generally falls within the range from about 0.5% to about 25%, more preferably about 1% to about 15%, even more preferably about 5% to about 10% by weight of the final composition.

The term "patient" or "subject" is used throughout the specification to describe an animal, generally a human, to whom administration of the compositions according to the present invention is provided.

The term "solvent free" is used to describe compositions according to the the present invention which avoid the inclusion of solvents such as polyhydric alcohols such as propylene glycol or glycerol. It is an unexpected result that compositions according to the present invention may be formulated without a solvent and yet produce a liquid dosage form which exhibits high bioavailability by virtue of its exceptionally high dissolution characteristics. Compositions according to the present invention in oral dosage form exhibit dissolution characteristics such that at least about 50% of the ubiquinone in the composition when subjected to the U.S.P. dissolution test will pass through a 0.45 micron filter. In certain preferred aspects according to the present invention, the dissolution of ubiquinone in the U.S.P. dissolution test will be at least about 90%, preferably at least about 95% and in some preferred embodiments, the dissolution in the U.S.P. dissolution test will approach 100%.

The term "effective amount" is used throughout the specification to describe concentrations or amounts of compounds or components according to the present invention which are added to produce an intended effect or used to produce a favorable result, whether that result relates to a composition's therapeutic or physiological effect or its ability to function for an alternative intended use, for example, a surfactant, glyceryl ester, triglyceride or a phospholipid or tocopherol (including vitamin E or vitamin E ester) which promotes the solubility of the ubiquinone or other bioactive agent.

The terms "triglycerides" and "vegetable oil" are used synonymously throughout the specification to describe an additive in compositions according to the present invention which may serve as a solubilizer or a compatibilizer of the ubiquinone with the other components of the present invention. This term is used as it is used by those of ordinary skill in the art, wherein fatty acids are esterifed at the free hydroxyl positions of glycerine, producing triglycerides, which are also the primary component of vegetable oils. Preferred triglycerides for use in the present compositions include vegetable oils including "medium chain triglycerides", which are tri-fatty esters of glycerol wherein the chain length of the fatty acids range from about 10–18 carbon units. Triglycerides are used as solubilizers, diluents and excipients, to compatabilize the formulations and promote uniformity. They are also integral to solubilization of the ubiquinone and further compatabilization with the phospholipid component of the present invention which results in the masking of the unpleasant taste of ubiquinone.

Vegetable oils for use in the present invention may include, for example, triglycerides which may be natural or synthetic (derived from esterification of glycerol and at least one organic acid, saturated or unsaturated, such as for example, such as butyric, caproic, palmitic, stearic, oleic, linoleic or linolenic acids, among numerous others, preferably a fatty organic acid, comprising between 8 and 26 carbon atoms). Glyceride esters for use in the present invention include vegetable oils derived chiefly from vegetables, seeds or nuts and include, for example, soybean, sunflower, safflower and cottonseed oil; non-drying oils, for example castor and coconut oil; and other oils, such as, for example, palm oil. Hydrogenated vegetable oils also may be used in the present invention. Animal oils are also contemplated for use as glyceride esters and include, for example, fats such as tallow, lard and stearin and liquid fats, such as fish oils, fish-liver oils and other animal oils, including sperm oil, among numerous others. In addition, a number of other oils may be used, including $C_{12}$ to $C_{30}$ (or higher) fatty esters (other than the glyceride esters, which are described above) or any other pharmaceutically acceptable triglyceride.

The amount of triglyceride used in the present invention ranges from about 0.1% to about 35% by weight, more preferably about 1.5% to about 25% by weight, even more preferably about 10% to about 25% by weight.

The term "bioactive agent" is used throughout the specification to a compound in addition to ubiquinone (i.e., other than a coenzyme Q analog) which is added to the composition in an effective amount. Bioactive agents for use in the present invention may include for example, reduced glutathione, L-cysteine, N-acetyl cysteine, reduced alpha-lipoic acid (DHLA), tocotrienols, tocopherols, including vitamin E and vitamin E esters, vitamin c (ascorbate) and vitamin c esters, vitamin A (retinol, retinoic acid) and vitamin A esters, carotenoids, including alpha carotene, beta carotene, lutein, zeaxanthin, astaxanthin, lycopene, flavonoids, L-carnitine, acetyl L-carnitine, propionyl L-carnitine, magnesium, zinc, selenium, manganese, riboflavin, niacinamide, curcuminoids, proanthocyanidins from grape seed extract and pine bark extract, NADH, NADPH, resveratrol, bilberry extract, milk thistle extract and omega-3-fatty acids from for example, fish oils and marine lipid concentrate). In certain aspects according to the present invention, the bioactive agent may be lipid soluble, for example, α-tocopherol (vitamin E), tocopherol esters, ascorbate esters such as ascorbyl palmitate, among others, alpha carotene and βP-carotene, lycopene, flavonoids, riboflavin, curcuminoids, retinol (vitamin A), retinoic acid, retinoic acid esters, retinol acetate, retinal and related bioactive agents, preferably those which may also be used as additives in dietary supplements. In certain preferred aspects of the present invention, the lipid soluble components may be used to enhance solubility of ubiquinone in the formulations. This is expecially true for the tocopherols, including the tocopherol esters where the amount included in compositions according to the present invention ranges from about 0.01% to about 25%, preferably about 5% to about 20%, even more preferably about 10% to about 20% by weight of the composition.

Especially preferred bioactive agents for inclusion as optional agents in compositions according to the present invention may include, for example, HMG CoA reductase inhibitors such as the statin drugs, for example, lovastatin, pravastatin, fluvastatin, simvastatin, mevastatin, fluindostatin, atorvastatin, cerivastatin, compactin among others, for their cholesterol lowering and triglyceride regulating effects, L-carnitine, acetyl L-carnitine and propionyl L-carnitine; alpha lipoic acid (thioctic acid) or reduced alpha lipoic acid; omega-3 fatty acids, tocotrienols and tocopherols. Whereas the statin drugs are included in compositions according to the present invention to produce down regulation of cholesterol and triglyceride levels, the combination of ubiquinone and the statin drugs are particularly effective for benefitting heart patients especially those with ischemia, ischemic or dilated cardiomyopathy, or those patients at risk for suffering a first or subsequent heart attack or who are at risk of having a stroke. Compositions which comprise effective amounts of L-carnitine, acetyl-L-carnitine and propionyl L-carnitine are also particularly useful for treating patients with anoxia, including myocardial anoxia and cerebellar anoxia, among others. Compositions which comprise ubiquinone and alpha lipoic acid (thioctic acid) are particularly useful for influencing glucose metabolism and treating diabetes, as well as enhancing a patient's immune response as well as reducing inflammation. Compositions according to the present invention which include omega-3 fatty acids are especially useful in treating coronary disease as well as substantially reducing the risk that a patient at risk will suffer a first or subsequently heart attack. In addition, such compositions are useful in down regulating triglycerides in the blood. Compositions according to the present invention which include tocotrienols and/or tocopherols are useful for reducing cholesterol levels in patients and treating patients with heart disease including those patients at risk for suffering a first or subsequent heart attack or who are at risk of having a stroke. Compositions according to the present invention utilize an effective amount of a bioactive agent other than ubiquinone within the range from about 0.01% to about 20% by weight, more preferably about 0.5% to about 10% by weight of the composition.

The present invention relates to a liquid dosage composition comprising:
 i. Ubiquinone in an effective amount, preferably an effective amount within the range from about 0.05% to about 15% by weight of the composition;
 ii. An effective amount of a primary surfactant falling within the range of about 0.1% to about 50% by weight, preferably about 1.5% to about 50% by weight of the composition, more preferably about 20% to about 50% by weight;
 iii. An effective amount of a glyceryl ester, more preferably a diester or triester, even more preferably a triester, within the range of about 0.1% to about 60% by weight, more preferably about 5% to about 30% by weight;
 iv. A triglyceride in an amount ranging from about 0.1% to about 35% by weight of the composition;
 iv. A phospholipid in an effective amount ranging from about 0% to about 25% by weight, preferably about 1.0% to about 15% by weight; and
 v. An amount of an optional secondary bioactive agent (other than ubiquinone or an analog thereof) in an effective amount preferably ranging from about 0% to about 20%, more preferably about 0.01% to about 25% by weight of the composition.

Compositions according to the present invention evidence an enhanced bioavailabilitiy of ubiquinone orally and topically, without the necessity of including a polyhydric alcohol solvent such as propylene glycol or glycerol. Given the relative insolubility of ubiquinone, especially Coenzyme $Q_{10}$, it is an unexpected result that compositions according to the present invention could be readily solubilized to produce liquid compositions characterised by exceptionally high dissolution and enhanced bioavailability which can be formulated into a wide variety of topically and orally administered compositions without the necessity of adding a polyhydric alcohol or other solvent.

In alternative embodiments, the compositions according to the present invention may include one or more of the following: a secondary surfactant such as a Span™ surfactant in an effective amount (preferably ranging from about 0.01% to about 7.5% by weight of the composition), and flavoring and coloring agents in minor amounts, generally ranging from about 0.005% to about 5% by weight of the final composition.

In certain embodiments according to the present invention, a pharmaceutically acceptable gelling agent or viscosity control agent, such as cellulose gelling agent (hydroxymethylcellulose, hydroxypropylcellulose, among others), guar gum, xanthan gum, etc., among numerous other pharmaceutically acceptable gelling agents may also be added to the compositions in amounts ranging from about 0.005% to about 3.0% by weight in an effort to produce a final composition which exhibits increased viscosity. Pharmaceutically acceptable carriers, additives and excipients which are appropriate for oral dosage forms may also be included within the compositions according to the present invention Compositions according to the present invention are formulated in cosmetic compositions, dietary supplements and pharmaceutical dosage forms. The compositions according to the present invention are generally delivered to the patient or subject orally or topically. When delivered orally, they are delivered as oral dosage forms pursuant to an appropriate pharmaceutical regimen. These oral dosage forms may include hard or soft gelatin capsules as well as tablets, powders or elixirs, among others.

In addition to oral dosage forms of ubiquinone, the present invention also contemplates compositions which may be used as topically administered creams or lotions for the treatment of wrinkles and other conditions of the skin (dermal conditions) where coenzyme Q exhibits an effect, suppositories for rectal or vaginal administration of ubiquinone, lozenges, gum, mouth rinse and toothpaste formulations, the gum and toothpaste forms especially for use in treating and/or preventing periodontal disease.

Compositions according to the present invention may be used for treatment of heart ailments and diseases such as congestive heart failure, high blood pressure, mitochochondrial disorders, including mitochondrial encephalomyopathy, anoxia, lactic acidosis, strokelike symptoms, neurodegenerative diseases, Kearns-Sayre syndrome and Alper's disease. Compositions according to the present invention may also be used to deter and/or treat periodontal disease, as well as lower elevated cholesterol levels in patients and to strengthen a weakened immune system as well as regulate (generally by reducing) the triglycerides in the blood. In addition, the use of ubiquinone to aid in the prevention of reperfusion injury of the heart is another potential use of the present invention. Compositions according to the present invention may optionally comprise an effective amount of an additional bioactive agent such as a vitamin or other therapeutic agent which acts to enhance the effects of ubiquinone (in some cases, synergistically) in treating or reducing the effects of a disease state, condition or ailment. Using the compositions according to the present invention are also contemplated by the present invention.

To prepare the pharmaceutical compositions according to the present invention, an effective amount of ubiquinone in powdered or liquid form is added to a mixture of a polysorbate surfactant (Tween™), glyceryl ester and triglycide at elevated temperature. A solvent may be optionally added. After thorough mixing, the remaining components are added to the mixture and mixed to a uniform consistency. Other components such as flavoring agents, coloring agents, preservatives and gelling agent, if applicable, may be added to the composition.

In preferred embodiments, compositions according to the present invention are produced by adding ubiquinone to a pre-mixed solution of surfactant, glyceryl ester and triglyceride (and optionally, vitamin E or a vitamin E ester) at elevated temperature (generally, at a temperature of about 45–80° C., preferably at a temperature of about 50–60° C.) until the components are thoroughly mixed. At the point of thorough mixing at elevated temperature, the components are in a liquid state. Subsequent to mixing of the components, coenzyme Q is added to the mixture at elevated temperature as described above and throughly mixed into the above components for a sufficient period, and the mixture can be used, upon further processing and the addition of additional bioactive agents, flavoring agents, gelling agents and the like to provide dosage forms which contain ubiquinone.

The concentration of ubiquinone to be included in the compositions according to the present invention is an effective amount for treating the patient's disease or condition. This concentration will depend on absorption, distribution, inactivation, and excretion rates of the ubiquinone and its metabolites as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient, ubiquinone, may be administered at once, or may be divided into a number of smaller doses to be administered at varying intervals of time.

The active components of the present invention can also be mixed with other active materials such as vitamin E (tocopherols) alcohol and vitamin E esters (acetate), alpha Lipoic acid, L-carnitine (and its derivatives acetyl-L-carnitine and propionyl-L-carnitine) and vitamins and minerals and other components, including omega-3-fatty acids, among others, which do not impair their desired action, or with materials that supplement the desired action provided that the added materials do not change the activity of the included compounds.

Oral administration is generally from one to four times daily. The most effective dosage form will depend upon the pharmacokinetics of the particular agent chosen as well as the severity of the condition in the patient to be treated.

The present compositions are used to treat any number of disease states or conditions which respond to the administration of ubiquinone. However, because the oral compositions increase the patient compliance of children, the treatment of childhood conditions or disease states will most likely find the greatest benefit in improved patient compliance using the compositions according to the present invention. The compositions according to the present invention are most preferably used to treat patients for heart disease, including congestive heart failure, high blood pressure, mitochochondrial disorders, including mitochondrial encephalomyopathy and other mitochondrial cytopathies, anoxia, lactic acidosis, neurodegenerative diseases, Kearns-Sayre syndrome and Alper's disease. Most preferably, the patient is a child and the condition or disease state is mitochondrial cytopathy.

Compositions according to the present invention are preferably formulated in oral dosage form, such as in tablets and capsules, even more preferably in hard or soft gelatin capsules, even more preferably in soft gelatin capsules, as the oral dosage form. The gelatin capsule is generally taken by the subject orally. It is an unexpected result that the ubiquinone from the liquid compositions according to the present invention results in a significantly enhanced bioavailability.

In addition to oral dosage forms, in certain preferred formulations, the liquid compositions may be formulated for use in creams and lotions to treat conditions of the skin such as wrinkles and suppositories for rectal and/or vaginal delivery of coenzyme Q. In the case of lozenges, gum, mouth rinse and toothpaste, these formulations may be used generally for systemic delivery of coenzyme Q or locally, primarily for the treatment of periodontal and related gum diseases.

Compositions according to the present invention may also include a pharmaceutically acceptable carrier, excipient or additive. Care must be taken to avoid having any one or more of these optional ingredients impact the solubility characteristics of the ubiquinone and other components in the composition.

The solubilized composition containing ubiquinone, in its preferred liquid form is water-free and therefore, suitable for use in oral dosage form, preferably, in gelatin capsules, which are prepared by conventional means as those skilled in the art would readily recognize. In preferred embodiments according to the present invention soft gelatin capsules are used, although two-piece hard gelatin capsules may be used (especially where the liquid composition at elevated temperature solidifies at room temperature). Hard gelatin capsules for use in the present invention are those which are well known in the art and comprise gelatin or hydroxypropylmethyl cellulose or a related cellulosic material in combination with glycerin. Any other acceptable formula which is well known in the art may also be used to provide two piece hard gelatin capsules. Soft gelatin capsules may comprise, for example, gelatin, glycerin and sorbitol as well as other components which are well known in the art. The gelatin capsules are generally tasteless, easy to swallow and they readily dissolve in the gastric juices of the digestive tract.

Alternatively, the compositions according to the present invention may be provided in tablet form using conventional tabletting methods well known in the art, for example, by adsorbing the composition onto a suitable solid carrier or excipient. The compositions according to the present invention can also be provided in a microencapsulated free flowing form. Enteric coated capsules or tablets are also contemplated by the present invention in order to enhance delivery of ubiquinone from the upper gastrointestinal tract (primarily, the duodenum where most of the absorption occurs). Enteric coating capsules may be produced by coating a tablet with composition containing, for example, hypromellose phthalate, diethyl phthalate, polyethylene glycol or any other suitable composition containing pharmaceutically acceptable enteric coating ingredients. One of ordinary skill using standard pharmaceutical formulation and packaging practices will be able to readily prepare any one or more of the oral dosage forms according to the present invention.

Alternatively, in certain preferred formulations, the compositions may be formulated for use in creams and lotions to treat conditions of the skin such as wrinkles using standard cosmetic and personal care product formulation techniques. In the case of suppositiories, compositions according to the present invention may be used in combination with an effective amount of a thickening agent to produce a formulation in suppository delivery form for rectal and/or vaginal delivery of delivery of coenzyme Q. In the case of lozenges, gum, mouth rinse and toothpaste, these formulations are produced preferably to be used for the treatment of periodontal and related gum diseases. In each instance where particular formulation is to be used, standard formulary processes and additives may be used to produce the desired dosage form. The requisite types and amounts of additives, such as thickeners, additional surfactants and/or solvents, flavors, coloring agents, emollients, humectants, fillers, and additional biologically active compounds (such as anti-caries agents and the like), etc. will be used in combination with a base formulation to produce the desired final products.

The concentration of ubiquinone in the compositions according to the present invention will depend on absorption, distribution, inactivation, and excretion rates of the ubiquinone and its metabolites as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient, ubiquinone, may be administered at once, or may be divided into a number of smaller doses to be administered at varying intervals of time.

The active compound of the present invention can also be mixed with other active materials that do not impair the desired action, or with materials that supplement the desired action provided that the added materials do not change the activity of the included compounds.

Administration of the active may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration. Enteric coated oral tablets, as an alternative to soft or hard gelatin capsules, may also be used to enhance bioavailability of the compounds from an oral route of administration. The most effective dosage form will depend upon the pharmacokinetics of the particular agent chosen as well as the severity of the condition in the patient to be treated. Oral dosage forms are particularly preferred, because of ease of administration and prospective favorable patient compliance. Creams and lotions are preferred where skin conditions, especially wrinkles, are to be treated. Lozenges, gums, mouth rinse and toothpaste are preferred where periodontal disease and other conditions of the patient's gums are to be treated.

Having generally described the invention, reference is now made to the following examples which are intended to illustrate preferred embodiments and comparisons. The included examples are not to be construed as limiting the scope of this invention as is more broadly set forth above and in the appended claims.

Example 1
Liquid Dosage Form of Coenzyme $Q_{10}$

| Wt. Range | Typical Syrup Rx | w/w |
|---|---|---|
| (0.05–15.0%) | Coenzyme $Q_{10}$ | 7% |
| (0.1%–50%) | Tween 80 (Polysorbate 80) | 38% |
| (0.1%–50%) | Tributyrin (Glyercyl tributyrate) | 19% |
| (0.5%–35%) | Medium Chain Triglycerides | 19% |
| (0.01–25%) | Vitamin E Alcohol (or acetate) | 17% |

This formulation results in 100% dissolution.

Formulation Procedure:
1. Add Tributyrin to the Medium Chain Triglycerides in a jacketed mixing vessel. Heat to 130° F. (±5° F.) with constant stirring at 160° ± RPM for approximately 2 hours or until dissolved.
2. Add Tween 80 to the above solution with constant stirring while maintaining the temperature at 130° F. (±5° F.). Keep mixing for at least 60 minutes.
3. Now screen the $CoQ_{10}$ powder through a 100 mesh screen into the liquid blend while stirring and maintaining the temperature at 130° F. (±5° F.). Keep stirring until a clear solution is obtained (about 60 minutes to 90 minutes). Then add the vitamin E alcohol or acetate and stir for an additional 30 minutes.
4. Remove the source of heat. Keep mixing while the temperature of the composition comes down to 100° F. At this point, add the flavoring solution. Mix for two hours.
5. Filter the finished syrup through a suitable filter.
6. Store formulation in air and light resistant container.
7. Test for assay of $CoQ_{10}$, dissolution of $CoQ_{10}$, color, clarity, etc.

Example 2
Liquid Dosage Form of Coenzyme $Q_{10}$

| Wt. Range | Typical Syrup Rx | w/w |
|---|---|---|
| (0.05–15.0%) | Coenzyme $Q_{10}$ | 7% |
| (0.1%–50%) | Tween 80 (Polysorbate 80) | 29% |
| (0.1%–50%) | Tributyrin (Glyercyl tributyrate) | 19% |
| (0.5%–35%) | Medium Chain Triglycerides | 20.5% |
| (0.0–25%) | Hydroxylated Lecithin (or High PC Lecithin) | 9.5% |
| (0.01–25%) | Vitamin E Alcohol (or acetate) | 15% |

This formulation results in 100% dissolution.

Formulation Procedure:
1. Add Tributyrin to the Medium Chain Triglycerides in a jacketed mixing vessel. Heat to 130° F. (±5° F.) with constant stirring at 160 +RPM for approximately 2 hours or until dissolved.
2. Add Tween 80 to the above solution with constant stirring while maintaining the temperature at 130° F. (±5° F.).

Keep mixing at same agitation speed as above for at least 60 minutes. Add the hydroxylated lecithin while stirring for a period of approximately 90 minutes.
3. Screen oQ$_{10}$ powder through a 100 mesh screen into the liquid blend while stirring and maintaining the temperature at 130° F. (±5° F.). Keep stirring until a clear solution is obtained (about 60 minutes to 90 minutes). Then add the vitamin E alcohol or acetate and stir for an additional 30 minutes.
4. Remove the source of heat. Keep mixing while the temperature of the composition comes down to 100° F. At this point, add the flavoring solution. Mix for two hours.
5. Filter the finished syrup through a suitable filter.
6. Store formulation in air and light resistant container.
7. Test for assay of CoQ$_{10}$, dissolution of CoQ$_{10}$, color, clarity, etc.

It is to be understood by those skilled in the art that the foregoing description and examples are illustrative of practicing the present invention, but are in no way limiting. Variations of the detail presented herein may be made without departing from the spirit and scope of the present invention as defined by the following claims.

What is claimed is:
1. An orally compatible composition in liquid dosage form consisting essentially of:
   i. An effective amount of ubiquinone;
   ii. An effective amount of a primary surfactant within the range of about 0.1% to about 50% by weight of said composition;
   iii. An effective amount of a glyceryl ester having the general structure:

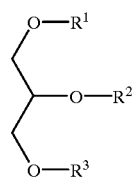

Where R$^1$, R$^2$ and R$^3$ are H or a C$_2$ to C$_7$ acyl group, with the proviso that at least one R$^1$ is an acyl group, said glyceryl ester being included in said formulation within the range of about 0.1% to about 60% by weight of said composition;
   iv. A triglyceride in an amount ranging from about 0.1% to about 25% by weight of the composition;
   v. A phospholipid in an amount ranging from about 0% to about 25% by weight; and
   vi. An amount of a secondary bioactive agent other than ubiquinone or ubiquinol ranging from about 0% to about 25% by weight of said composition.

2. The composition according to claim 1 wherein said primary surfactant is a polysorbate surfactant in an amount ranging from about 1.5% to about 50% by weight of said composition.

3. The composition according to claim 1 wherein said triglyceride is a mixture of medium chain triglycerides comprising about 5% to about 35% by weight of said composition.

4. The composition according to claim 1 wherein said phospholipid is selected from the group consisting of phosphatidylcholine, phosphatidylethanolamine, hydroxylated lecithin, distearoylphosphatidylcholine, phosphatidylserine, phosphatidylglycerol, phosphatidic acid, phosphatidylinositol, sphingomyelin, dimyristoylphosphatidylcholine, dimyristoylphosphatidylglycerol, and mixtures thereof and comprises about 1% to about 20% by weight of said composition.

5. The composition according to claim 4 wherein said phospholipid is hydroxylated lecithin in an amount ranging from about 1% to about 15% by weight.

6. The composition according to claim 1 wherein said secondary bioactive agent is selected from the group consisting of α-tocopherol, tocopherol esters, ascorbate esters such as ascorbyl palmitate, among others, α-carotene, β-carotene, lycopene, flavonoids, riboflavin, curcuminoids, retinol, retinoic acid, retinoic acid esters, retinol acetate, retinal and mixtures, thereof.

7. The composition according to claim 1 further comprising an effective amount of at least one additional component selected from the group consisting of flavorings, coloring agents gelling agents and a secondary surfactant.

8. The composition according to claim 1 wherein said secondary bioactive agent is selected from the group consisting of tocopherols, alpha lipoic acid, L-carnitine, acetyl-L-carnitine, propionyl-L-carnitine, omega-3-fatty acids, vitamins, minerals and mixtures, thereof.

9. The composition according to claim 1 wherein said primary surfactant is polysorbate 80 in an amount ranging from about 20% to about 50% by weight of said composition, said glyceryl ester is selected from the group consisting of glyceryl triacetate, glyceryl tributyrate and mixtures thereof comprising about 5% to about 30% by weight of said composition, said triglyceride is a mixture of medium chain triglycerides comprising about 5% to about 35% by weight of said composition and said phospholipid is hydroxylated lecithin comprising about 1% to about 10% by weight of said composition.

10. An orally compatible composition in liquid dosage form comprising:
   i. An effective amount of coenzyme Q$_{10}$;
   ii. An effective amount of a polysorbate surfactant ranging from about 1.5% to about 50% by weight;
   iii. An effective amount of a glyceryl ester having the general structure:

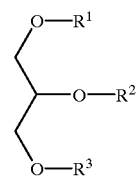

Where R$^1$, R$^2$ and R$^3$ are H or a C$_2$ to C$_7$ acyl group, with the proviso that at least one R$^1$ is an acyl group, said glyceryl ester being included in said formulation within the range of about 0.1% to about 60% by weight of said composition;
   iv. A mixture of medium chain triglycerides ranging from about 5% to about 35% by weight of the composition;
   v. Hydroxylated lecithin as a phospholipid in an effective amount ranging from about 0% to about 25% by weight of said composition; and
   vi. An amount of a secondary bioactive agent other than ubiquinone or an analog of ubiquinone ranging from about 0% to about 25% by weight of said composition;
Wherein said composition is free of polyhydric alcohol solvents.

11. The composition according to claim 10 wherein said secondary bioactive agent is selected from the group consisting of reduced glutathione, L-cysteine, N-acetyl cysteine, reduced alpha-lipoic acid (DHLA), tocotrienols, tocopherols, including vitamin E and vitamin E esters, vitamin c (ascorbate) and vitamin c esters, vitamin A (retinol, retinoic acid) and vitamin A esters, carotenoids, including alpha carotene, beta carotene, lutein, zeaxanthin, astaxanthin, lycopene, flavonoids, L-carnitine, acetyl L-carnitine, propionyl L-carnitine, magnesium, zinc, selenium, manganese, riboflavin, niacinamide, curcuminoids, proanthocyanidins from grape seed extract and pine bark extract, NADH, NADPH, resveratrol, bilberry extract, milk thistle extract, omega-3-fatty acids, α-tocopherol, tocopherol esters, ascrobic acid, ascorbate esters, alpha carotene, β-carotene, lycopene, flavonoids, riboflavin, curcuminoids, retinol, retinoic acid, retinoic acid esters, lovastatin, pravastatin, fluvastatin, simvastatin, mevastatin, fluindostatin, atorvastatin, cerivastatin, compactin, L-carnitine, acetyl L-carnitine, propionyl L-carnitine; alpha lipoic acid (thioctic acid) or reduced alpha lipoic acid; omega-3 fatty acids, tocotrienols and mixtures thereof.

12. The composition according to claim 11 wherein said polysorbate surfactant is polysorbate 80 in an amount ranging from about 20% to about 50% by weight.

13. The composition according to claim 11 further comprising a phospholipid selected from the group consisting of phosphatidylcholine, phosphatidylethanolamine, hydroxylated lecithin, distearoylphosphatidylcholine, phosphatidylserine, phosphatidylglycerol, phosphatidic acid, phosphatidylinositol, sphingomyelin, dimyristoylphosphatidylcholine, dimyristoylphosphatidylglycerol, and mixtures thereof in an amount ranging from about 1% to about 20% by weight of said composition.

14. The composition according to claim 12 wherein said phospholipid is hydroxylated lecithin in an amount ranging from about 1% to about 15% by weight of said composition.

15. The composition according to claim 11 wherein said secondary bioactive agent is selected from the group consisting of α-tocopherol, tocopherol esters, ascorbate esters, α-carotene, β-carotene, lycopene, flavonoids, riboflavin, curcuminoids, retinol, retinoic acid, retinoic acid esters, retinol acetate, retinal and mixtures, thereof.

16. The composition according to claim 11 further comprising an effective amount of at least one additional component selected from the group consisting of flavorings, coloring agents, gelling agents and a secondary surfactant.

17. The composition according to claim 11 wherein said secondary bioactive agent is selected from the group consisting of tocopherols, alpha lipoic acid, L-carnitine, acetyl-L-carnitine, propionyl-L-carnitine, omega-3-fatty acids, vitamins, minerals and mixtures, thereof.

18. An orally compatible composition in liquid dosage form consisting essentially of:
   i. An effective amount of ubiquinone;
   ii. An effective amount of a primary surfactant within the range of about 0.1% to about 50% by weight of said composition;
   iii. An effective amount of a glyceryl ester having the general structure:

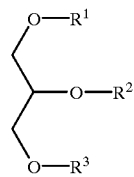

Where $R^1$, $R^2$ and $R^3$ are H or a $C_2$ to $C_7$ acyl group, with the proviso that at least one $R_1$ is an acyl group, said glyceryl ester being included in said formulation within the range of about 0.1% to about 60% by weight of said composition;
   iv. A triglyceride in an amount ranging from about 0.1% to about 25% by weight of the composition;
   v. A phospholipid in an amount ranging from about 0% to about 25% by weight;
   vi. An amount of a tocopherol or an ester of tocopherol ranging from about 0.01% to about 25% by weight of said composition; and
   vii. An amount of a secondary bioactive agent other than ubiquinone or ubiquinol ranging from about 0% to about 25% by weight of said composition.

19. The composition according to claim 18 wherein said primary surfactant is a polysorbate surfactant in an amount ranging from about 1.5% to about 50% by weight of said composition.

20. The composition according to claim 18 wherein said triglyceride is a mixture of medium chain triglycerides comprising about 5% to about 35% by weight of said composition.

21. The composition according to claim 18 wherein said phospholipid is selected from the group consisting of phosphatidylcholine, phosphatidylethanolamine, hydroxylated lecithin, distearoylphosphatidylcholine, phosphatidylserine, phosphatidylglycerol, phosphatidic acid, phosphatidylinositol, sphingomyelin, dimyristoylphosphatidylcholine, dimyristoylphosphatidylglycerol, and mixtures thereof and comprises about 1% to about 20% by weight of said composition.

22. The composition according to claim 21 wherein said phospholipid is hydroxylated lecithin in an amount ranging from about 1% to about 15% by weight.

23. The composition according to claim 18 wherein said secondary bioactive agent is selected from the group consisting of ascorbate esters such as ascorbyl palmitate, among others, α-carotene, β-carotene, lycopene, flavonoids, riboflavin, curcuminoids, retinol, retinoic acid, retinoic acid esters, retinol acetate, retinal and mixtures, thereof.

24. The composition according to claim 18 further comprising an effective amount of at least one additional component selected from the group consisting of flavorings, coloring agents gelling agents and a secondary surfactant.

25. The composition according to claim 18 wherein said secondary bioactive agent is selected from the group consisting of tocopherols, alpha lipoic acid, L-carnitine, acetyl-L-carnitine, propionyl-L-carnitine, omega-3-fatty acids, vitamins, minerals and mixtures, thereof.

26. The composition according to claim 18 wherein said primary surfactant is polysorbate 80 in an amount ranging from about 20% to about 50% by weight of said composition, said glyceryl ester is selected from the group consisting of glyceryl triacetate, glyceryl tributyrate and mixtures thereof comprising about 5% to about 30% by weight of said composition, said triglyceride is a mixture of medium chain triglycerides comprising about 5% to about 35% by weight of said composition and said phospholipid is hydroxylated lecithin comprising about 1% to about 10% by weight of said composition.

27. An orally compatible composition in liquid dosage form comprising:
  i. An effective amount of coenzyme $Q_{10}$;
  ii. An effective amount of a polysorbate surfactant ranging from about 1.5% to about 50% by weight;
  iii. An effective amount of a glyceryl ester having the general structure:

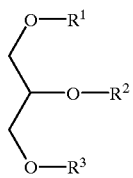

Where $R^1$, $R^2$ and $R^3$ are H or a $C_2$ to $C_7$ acyl group, with the proviso that at least one $R^1$ is an acyl group, said glyceryl ester being included in said formulation within the range of about 0.1% to about 60% by weight of said composition;
  iv. A mixture of medium chain triglycerides ranging from about 5% to about 35% by weight of the composition;
  v. Hydroxylated lecithin as a phospholipid in an effective amount ranging from about 0% to about 25% by weight of said composition;
  vi. An amount of a tocopherol or an ester of tocopherol ranging from about 0.01% to about 25% by weight of said composition; and
  vii. An amount of a secondary bioactive agent other than ubiquinone or an analog of ubiquinone ranging from about 0% to about 25% by weight of said composition;
Wherein said composition is free of polyhydric alcohol solvents.

28. The composition according to claim 27 wherein said secondary bioactive agent is selected from the group consisting of reduced glutathione, L-cysteine, N-acetyl cysteine, reduced alpha-lipoic acid (DHLA), tocotrienols, vitamin c (ascorbate) and vitamin c esters, vitamin A (retinol, retinoic acid) and vitamin A esters, carotenoids, including alpha carotene, beta carotene, lutein, zeaxanthin, astaxanthin, lycopene, flavonoids, L-carnitine, acetyl L-carnitine, propionyl L-carnitine, magnesium, zinc, selenium, manganese, riboflavin, niacinamide, curcurminoids, proanthocyanidins from grape seed extract and pine bark extract, NADH, NADPH, resveratrol, bilberry extract, milk thistle extract, omega-3-fatty acids, α-tocopherol, tocopherol esters, ascrobic acid, ascorbate esters, alpha carotene, β-carotene, lycopene, flavonoids, riboflavin, curcuminoids, retinol, retinoic acid, retinoic acid esters, lovastatin, pravastatin, fluvastatin, simvastatin, mevastatin, fluindostatin, atorvastatin, cerivastatin, compactin, L-carnitine, acetyl L-carnitine, propionyl L-carnitine; alpha lipoic acid (thioctic acid) or reduced alpha lipoic acid; omega-3 fatty acids, tocotrienols and mixtures thereof.

29. The composition according to claim 27 wherein said polysorbate surfactant is polysorbate 80 in an amount ranging from about 20% to about 50% by weight.

30. The composition according to claim 27 further comprising a phospholipid selected from the group consisting of phosphatidylcholine, phosphatidylethanolamine, hydroxylated lecithin, distearoylphosphatidylcholine, phosphatidylserine, phosphatidylglycerol, phosphatidic acid, phosphatidylinositol, sphingomyelin, dimyristoylphosphatidylcholine, dimyristoylphosphatidylglycerol, and mixtures thereof in an amount ranging from about 1% to about 20% by weight of said composition.

31. The composition according to claim 28 wherein said phospholipid is hydroxylated lecithin in an amount ranging from about 1% to about 15% by weight of said composition.

32. The composition according to claim 27 wherein said secondary bioactive agent is selected from the group consisting of ascorbate esters, α-carotene, β-carotene, lycopene, flavonoids, riboflavin, curcuminoids, retinol, retinoic acid, retinoic acid esters, retinol acetate, retinal and mixtures, thereof.

33. The composition according to claim 27 further comprising an effective amount of at least one additional component selected from the group consisting of flavorings, coloring agents, gelling agents and a secondary surfactant.

34. The composition according to claim 27 wherein said secondary bioactive agent is selected from the group consisting of tocopherols, alpha lipoic acid, L-carnitine, acetyl-L-carnitine, propionyl-L-carnitine, omega-3-fatty acids, vitamins, minerals and mixtures, thereof.

35. A method of increasing the bioavailability of ubiquinone from an orally delivered or topically delivered composition without the need to add solubilizing quantities of a polyhydric solvent to said composition, said method comprising formulating into a liquid dosage form to be incorporated into a cosmetic, dietary supplement or pharmaceutical dosage form a liquid composition comprising:
  i. An effective amount of ubiquinone;
  ii. An effective amount of a primary surfactant falling within the range of about 1.5% to about 50% by weight of said liquid composition;
  iii. An effective amount of a glyceryl triester having $C_2$ to $C_7$ acyl groups, said glyceryl triester being included in said composition in an amount ranging from about 5% to about 60% by weight of said composition;
  iv. A triglyceride in an amount ranging from about 0.1% to about 35% by weight of the composition;
  v. A phospholipid in an amount ranging from 0% to about 25% by weight; and
  vi. A secondary bioactive agent other than ubiquinone or ubiquinol in an amount ranging from 0% to about 25% by weight; and
incorporating said liquid composition into a cosmetic, dietary supplement or pharmaceutical dosage form.

36. The method according to claim 35 wherein said primary surfactant is polysorbate 80 included in an amount ranging from about 1.5% to about 50% by weight of said composition.

37. The method according to claim 35 wherein said triglyceride is a mixture of medium chain triglycerides comprising about 5% to about 35% by weight of said composition.

38. The method according to claim 35 wherein said phospholipid is selected from the group consisting of phosphatidylcholine, phosphatidylethanolamine, hydroxylated lecithin, distearoylphosphatidylcholine, phosphatidylserine, phosphatidylglycerol, phosphatidic acid, phosphatidylinositol, sphingomyelin, dimyristoylphosphatidylcholine, dimyristoylphosphatidylglycerol, and mixtures thereof and comprises about 1% to about 25% by weight of said composition.

39. The method according to claim 38 wherein said phospholipid is hydroxylated lecithin in an amount ranging from about 1% to about 15% by weight.

40. The method according to claim 35 wherein said composition further comprises an effective amount of at least one additional component selected from the group consisting of gelling agents, flavorings, coloring agents and a secondary surfactant.

41. The method according to claim 35 wherein said primary surfactant is polysorbate 80 in an amount ranging from about 20% to about 50% by weight of said composition, said triglyceride is a mixture of medium chain triglycerides comprising about 5% to about 35% by weight of said composition, said glyceryl triester is selected from the group consisting of glyceryl triacetate, glyceryl tributyrate and mixtures, thereof and said phospholipid is selected from the group consisting of phosphatidylcholine, phosphatidylethanolamine, hydroxylated lecithin, distearoylphosphatidylcholine, phosphatidylserine, phosphatidylglycerol, phosphatidic acid, phosphatidylinositol, sphingomyelin, dimyristoylphosphatidylcholine, dimyristoylphosphatidylglycerol, and mixtures thereof in an amount ranging from about 1% to about 25% by weight of said composition.

42. A method of increasing the bioavailability of ubiquinone from an orally delivered or topically delivered composition without the need to add solubilizing quantities of a polyhydric solvent to said composition, said method comprising formulating into a liquid dosage form to be incorporated into a cosmetic, dietary supplement or pharmaceutical dosage form a liquid composition comprising:

i. An effective amount of ubiquinone;
  ii. An effective amount of a primary surfactant falling within the range of about 1.5% to about 50% by weight of said liquid composition;
  iii. An effective amount of a glyceryl triester having $C_2$ to $C_7$ acyl groups, said glyceryl triester being included in said composition in an amount ranging from about 5% to about 60% by weight of said composition;
  iv. A triglyceride in an amount ranging from about 0.1% to about 35% by weight of the composition;
  v. A phospholipid in an amount ranging from 0% to about 25% by weight;
  vi. An amount of a tocopherol or an ester of tocopherol ranging from about 0.01% to about 25% by weight of said composition; and
  vii. A secondary bioactive agent other than ubiquinone or ubiquinol in an amount ranging from 0% to about 25% by weight; and incorporating said liquid composition into a cosmetic, dietary supplement or pharmaceutical dosage form.

43. The method according to claim 42 wherein said primary surfactant is polysorbate 80 included in an amount ranging from about 1.5% to about 50% by weight of said composition.

44. The method according to claim 42 wherein said triglyceride is a mixture of medium chain triglycerides comprising about 5% to about 35% by weight of said composition.

45. The method according to claim 42 wherein said phospholipid is selected from the group consisting of phosphatidylcholine, phosphatidylethanolamine, hydroxylated lecithin, distearoylphosphatidylcholine, phosphatidylscrine, phosphatidylglycerol, phosphatidic acid, phosphatidylinositol, sphingomyelin, dimyristoylphosphatidylcholine, dimyristoylphosphatidylglycerol, and mixtures thereof and comprises about 1% to about 25% by weight of said composition.

* * * * *

UNITED STATES PATENT AND TRADEMARK OFFICE
CERTIFICATE OF CORRECTION

PATENT NO. : 6,300,377 B1
DATED : October 9, 2001
INVENTOR(S) : Raj K. Chopra

It is certified that error appears in the above-identified patent and that said Letters Patent is hereby corrected as shown below:

Column 13,
Line 43, change "$R^1$" to -- at least one of $R^1$, $R^2$ and $R^3$ --.

Column 14,
Line 52, change "$R^1$" to -- at least one of $R^1$, $R^2$ and $R^3$ --.

Column 16,
Line 23, change "$R^1$" to -- at least one of $R^1$, $R^2$ and $R^3$ --.

Signed and Sealed this

Twelfth Day of October, 2004

JON W. DUDAS
*Director of the United States Patent and Trademark Office*

UNITED STATES PATENT AND TRADEMARK OFFICE
CERTIFICATE OF CORRECTION

PATENT NO. : 6,300,377 B1
DATED : October 9, 2001
INVENTOR(S) : Raj K. Chopra

It is certified that error appears in the above-identified patent and that said Letters Patent is hereby corrected as shown below:

Column 13,
Line 43, change "$R^1$" to -- at least one of $R^1$, $R^2$ and $R^3$ --.

Column 14,
Line 52, change "$R^1$" to -- at least one of $R^1$, $R^2$ and $R^3$ --.

Column 16,
Line 11, change "$R^1$" to -- at least one of $R^1$, $R^2$ and $R^3$ --.
Line 23, change "$R^1$" to -- at least one of $R^1$, $R^2$ and $R^3$ --.

Signed and Sealed this

Twenty-eighth Day of December, 2004

JON W. DUDAS
*Director of the United States Patent and Trademark Office*